United States Patent
Nedbal

[11] Patent Number: 5,180,643
[45] Date of Patent: Jan. 19, 1993

[54] HYDROMETER COLLAR IMPROVEMENT

[75] Inventor: Ralph G. Nedbal, Saint Charles, Ill.

[73] Assignee: Illinois Tool Works Inc., Glenview, Ill.

[21] Appl. No.: 807,243

[22] Filed: Dec. 16, 1991

[51] Int. Cl.$^5$ .......................................... H01M 10/48
[52] U.S. Cl. ...................................... 429/91; 215/355; 215/358
[58] Field of Search .................... 215/355, 358; 429/91

[56] References Cited

U.S. PATENT DOCUMENTS

| | | | |
|---|---|---|---|
| 533,153 | 1/1895 | Willard | 429/91 |
| 3,057,502 | 4/1958 | Wood | 215/355 |
| 3,095,009 | 6/1963 | Conley | 429/91 |
| 3,893,339 | 7/1975 | Melone | 73/327 |
| 4,308,817 | 1/1982 | Peterson | 429/91 |
| 4,413,744 | 11/1983 | Babiol | 215/355 |

FOREIGN PATENT DOCUMENTS 543994  5/1956  Italy ...................... 215/355

Primary Examiner—Olik Chaudhuri
Assistant Examiner—M. Nuzzolillo
Attorney, Agent, or Firm—Schwartz & Weinrieb

[57] ABSTRACT

An improved hydrometer collar for use within lead-acid storage batteries of the type installed within vehicles includes a cylindrically-shaped member having an annular side wall. A plurality of sealing rings are formed upon the outer surface of the annular side wall. Each one of the plurality of sealing rings is spaced axially apart from each other in a substantially parallel relationship so as to form annular grooves therebetween. A small wiping rib is formed integrally with each one of the plurality of sealing rings and extends radially outwardly therefrom. Each one of the wiping ribs is disposed substantially intermediate an upper surface and a lower surface of a corresponding one of the plurality of sealing rings. The wiping ribs are easily deformable so as to fill any imperfections existing upon the interior surface of a battery casing bore of the storage battery into which the collar is inserted thereby creating a fluid-tight seal therewith.

20 Claims, 2 Drawing Sheets

HYDROMETER COLLAR IMPROVEMENT

BACKGROUND OF THE INVENTION

1. Field of the Invention

This invention relates generally to hydrometer devices for use within lead-acid storage batteries of the type installed within vehicles and the like. More particularly, the present invention relates to a battery hydrometer collar having a novel sealing means so as to provide a better seal upon insertion of the hydrometer into a pre-formed bore located within the top of a battery casing.

2. Description of the Prior Art

A prior art search directed to the subject matter of this application in the U.S. Patent and Trademark Office revealed the following U.S. Letters Patent:

| | | |
|---|---|---|
| 1,262,478 | 729,835 | 3,338,447 |
| 1,410,929 | 2,669,370 | 3,405,830 |
| 2,093,669 | 2,704,100 | 3,898,046 |
| 2,117,170 | 2,746,632 | 4,230,231 |
| 3,223,269 | 2,927,709 | 4,253,581 |
| 3,754,445 | 2,993,612 | 4,883,641 |
| 4,052,534 | 3,057,502 | |

In accordance with a known hydrometer device of the prior art for use within lead-acid storage batteries to be installed within automobiles, the hydrometer device includes a cylindrically-shaped collar member, a light transmissive rod, and a cage having a float ball. The upper end of the rod is connected to the cylindrically-shaped member, and the lower end of the rod is connected to the cage. The cylindrically-shaped collar member is provided with external ribs for frictional engagement with a corresponding opening defined within the battery casing wall so as to define a sealing relationship therebetween. Such prior art hydrometer device is shown in U.S. Pat. No. 4,240,282 to John F. Nelson, which is assigned to the same assignee of the present invention.

The principal unsolved problem of this prior art hydrometer device is that it does not always provide a satisfactory seal and thus oftentimes leaks. In other words, a sufficient seal between the collar member and the interior wall of the bore of the battery casing so as to prevent leakage of the acid from within the storage battery cannot be maintained at all times. Generally, this is because of wide tolerances encountered in the internal diameters of the battery casing bore along its axial length when the battery casings are commercially produced in large quantities and into which the collar members have to be fitted. Furthermore, in the manufacture of the battery casing bores there are produced at times various imperfections such as, for example, scratches, voids and the like upon the interior surfaces thereof.

Another difficulty with this prior art hydrometer device arises during its insertion into the battery casing bore by means of automatic assembling machines. Such machines automatically insert or drop the hydrometer device into the battery casing bore as the batteries are moved by means of conveyor and thereafter a downward force is applied to the top of the collar member so as to secure the hydrometer device within the battery casing bore. If the hydrometer device is not properly aligned within the battery bore, then some of the external ribs upon the collar member will possibly be damaged or destroyed thereby preventing a fluid-tight seal. In the event of imperfect operation of diameters, this will inevitably result in a tendency for the acid to be leaked from the battery.

In U.S. Pat. No. 3,223,269 to Harold W. Williams issued on Dec. 14, 1965, there is disclosed a screw cap closure for bottles which includes an outer wall and a hollow cylindrical, plug-type sealing member. In order to protect against leakage, the sealing member is formed with a circular bead which will be yieldingly pressed into engagement with and conforms to any irregularities of the shape of the inner surface of the bottle.

In U.S. Pat. No. 4,052,534 to John L. Devitt issued on Oct. 4, 19877, there is disclosed a battery vent plug for insertion into a battery case vent well which includes an 0-ring gasket positioned around the outer cylindrical surface of a lower cylindrical member for engaging the interior walls of the battery case vent well. The 0-ring gasket provides a gas-type seal with respect to the vent well when the plug is disposed therein.

In accordance with U.S. Pat. No. 2,669,370 to Ivey G. Royall, Jr. issued on Feb. 16, 1954, there is taught a rubber stopper which includes a cylindrical outer wall portion and an inner end closed off by means of a wall. The outer peripheral surface of the wall portion is provided with two sets of first and second ribs. The first set of ribs are arranged at the top of the wall portion and are made continuous throughout the periphery of the wall portion. The second set of ribs are arranged at the lower end of the wall portion and are made discontinuous by means of passageways so as to permit air to escape from the bottle during the initial movement of the stopper its operative sealing position. Thereafter, the first ribs are moved into engagement with the inner neck portion of the bottle for effecting a complete seal.

U.S. Pat. No. 2,746,632 to Carl Bramming issued on May 22, 1956, discloses a flexible cup-shaped closure member for a vacuum bottle which has an annular side wall. The outer surfaces of the side wall is provided with a plurality of ribs which prevent any liquid within the vacuum bottle from escaping therefrom.

U.S. Pat. No. 2,927,709 to H. O. Hoffman et al. issued on Mar. 8, 1960, shows a bottle stopple which includes a main body section having two axially spaced portions located at its axially inner end and extending across a slot. The spaced portions are compressible in a radial direction for facilitating engagement thereof with the opening of the bottle. A rib is formed upon the axially inner end of the body section for temporarily holding the stopple in engagement with the bottle.

U.S. Pat. No. 2,993,612 to Erich Trautuetter issued on July 25, 1961, discloses a bottle stopper comprised of a sealing neck and a stopper jacket. The sealing neck has upon its outside face a plurality of sealing lips which provides a sealing function with respect to the inner pressure of the bottle. The sealing lips are arranged in a spaced-apart and parallel relationship with respect to each other and are formed as closed annular ribs.

Furthermore, there are disclosed a number of other patents in the prior art which also show various types of stoppers having ribs or ridges so as to provide fluidtight sealing of a container as evidenced by means of U.S. Pat. Nos. 3,057,502 to Wood; 3,338,447 to Meyers, Jr.; 3,405,830 to Hayashida; and 3,898,046 to Ikeda et al. The remaining patents uncovered from the search but not specifically discussed are merely cited to generally show the state of the art and are directed toward various types of hydrometer devices and stoppers for sealing containers.

The present invention represents a substantial improvement over the aforementioned U.S. Pat. No. 4,240,252 which is hereby incorporated by reference. The hydrometer collar of the present invention includes a cylindrically-shaped member having an annular side wall, a plurality of sealing rings being formed upon the outer surface of the annular side wall, and a small wiping rib being formed integrally with each one of the plurality of sealing rings and extending radially outwardly therefrom. The wiping ribs are easily deformable so as to fill any imperfections existing upon the interior surface of the battery casing bore into which the collar is inserted, thereby creating a fluid-tight seal.

OBJECTS OF THE INVENTION

Accordingly, it is a general object of the present invention to provide an improved hydrometer collar for use within lead-acid storage batteries of the type installed within vehicles and which is relatively simple and economical to manufacture and assemble, but yet overcomes the disadvantages of the prior art hydrometer devices.

It is also an object of the present invention to provide a battery hydrometer collar having a novel sealing means so as to permit a better seal to be achieved upon insertion of the hydrometer into a pre-formed bore located within the top of a battery casing.

It is another object of the present invention to provide an improved hydrometer collar for use within lead-acid storage batteries of the type installed within vehicles and which includes a cylindrically-shaped member having an annular side wall, a plurality of sealing rings being formed upon the outer surface of the annular side wall, and a small wiping rib being formed integrally with each one of the plurality of sealing rings and extending radially outwardly therefrom.

It is still another object of the present invention to provide an improved hydrometer collar for use within lead-acid storage batteries of the type installed within vehicles which includes a lead-in ring disposed upon the lower or axially-leading surface of a cylindrical member of the collar for assisting in alignment of the collar with respect to the battery bore during insertion of the collar into the battery bore.

SUMMARY OF THE INVENTION

In a preferred embodiment of the present invention, there is provided an improved hydrometer collar for use within lead-acid storage batteries of the type installed within vehicles which includes a cylindrically-shaped member having an annular side wall. A plurality of sealing rings are formed upon the outer surface of the annular side wall. Each one of the plurality of sealing rings are axially spaced from each other in a substantially parallel relationship so as to form annular grooves therebetween. A small wiping rib is formed integrally with each one of the plurality of sealing rings and extends radially outwardly therefrom. Each one of the wiping ribs is disposed substantially intermediate an upper surface and a lower surface of a corresponding one of the plurality of sealing rings. The wiping ribs are easily deformable so as to fill any imperfections existing upon the interior of a battery casing bore of the storage battery into which the collar is inserted thereby creating a fluid-tight seal.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, and wherein.

DESCRIPTION OF THE PREFERRED EMBODIMENT

Figures 1, 2, 3, 4, 5:
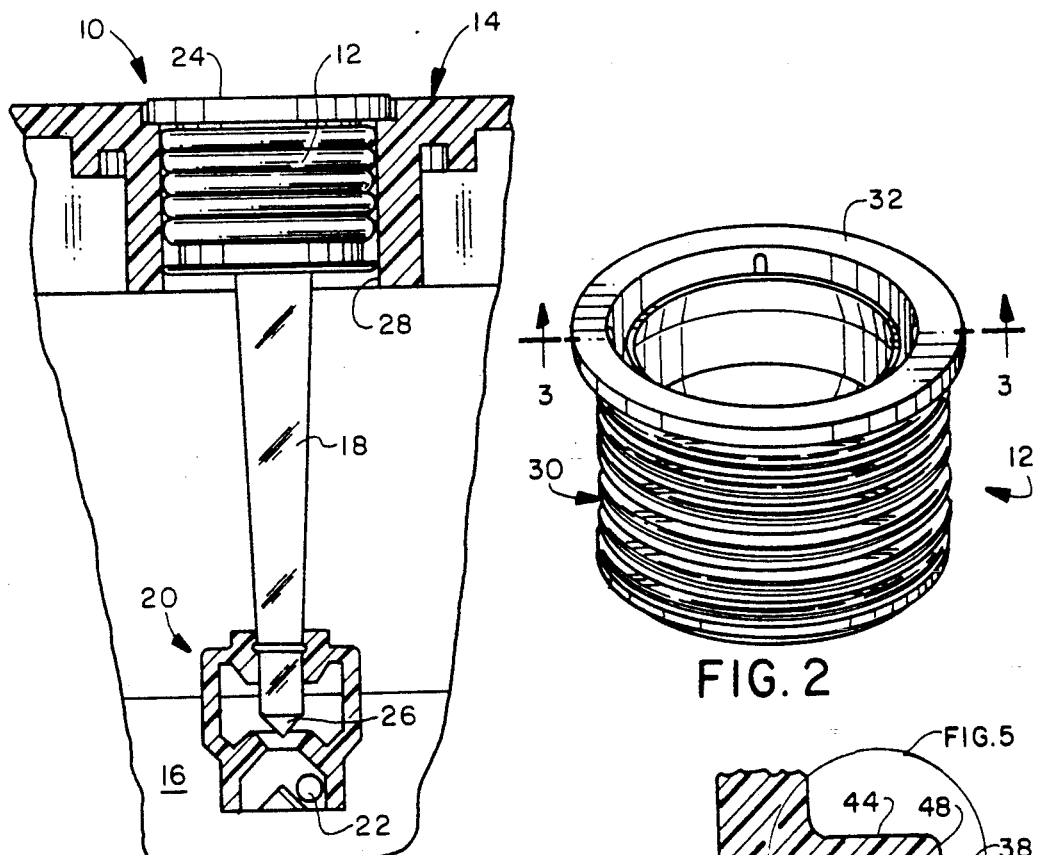
FIG. 1 is a front elevational view, partly in cross-section, of a hydrometer device embodying the improved collar of the present invention for use within a common automotive-type lead-acid storage battery.
FIG. 2 is a perspective view of the improved hydrometer collar of the present invention.
FIG. 3 is a cross-sectional view, taken along the lines 3—3 of FIG. 2.
FIG. 4 is an enlarged view of the encircled portion of FIG. 3.
FIG. 5 is an isolated view of the encircled portion of FIG. 4.

Referring now in detail to the various views of the drawings, there is shown in FIG. 1 a hydrometer device 10 embodying an improved collar 12 of the present invention for use within a typical automotive-type lead-acid storage battery 14. The hydrometer device 10 is utilized for checking both the level of a fluid electrolyte or liquid 16 subject to fluctuations and also the specific gravity of the liquid. The hydrometer device includes a light transmissive member or rod 18 which is formed from a light-transmitting material such as, for example, acrylic, glass, styrene or other clear or partially clear materials. The rod 18 is preferably elongated so that it may be mounted within a fluid vessel of the battery casing. The upper end of the rod 18 is connected to the improved hydrometer collar 12, and a lower end thereof is connected to a cage or chamber 20 which houses a float member 22.

The rod 18 further includes an indicating surface at its upper end 24 which is external to the storage battery 14 and a light-reflecting cone-shaped tip surface 26 which is arranged so as to be submerged within the liquid 16. The collar member 12 is adapted to fit snugly within a pre-formed bore 28 formed within the top of the battery casing so as to create a fluid-tight seal therewith. As is well-known to those skilled in the art, float member 22 is movable relative to the reflecting surface 26 for indicating the relative specific gravity of the liquid. In a first position, the float member 22 is viewable through the indicating surface at the upper end 24 of the rod for indicating that the specific gravity of the liquid is above a predetermined specific gravity value. In a second position, the float member is moved out of view from the reflecting surface 26 so that it cannot be observed through the indicating surface thereby indicating that the specific gravity of the liquid is below the predetermined specific gravity level or gravity.

The present invention is directed toward the improved collar member 12 of the hydrometer device 10 so as to facilitate a fluid-tight seal with respect to the bore of the battery casing upon insertion of the hydrometer device into the bore 28 of the battery casing. Since the other components of the hydrometer device do not form a part of the present invention, these components have been intentionally omitted from FIGS. 2 through 10 for the sake of clarity.

Referring now to FIGS. 2 and 3, the improved hydrometer collar 12 comprises a hollow, cylindrically-shaped member 30 extending downwardly from an upper circular flange 32 and having an annular side wall 34. A plurality of sealing rings 36a–36e, that is at least five, are formed upon the outer surface of the side wall 34 and are spaced axially apart from each other in a substantially parallel relationship so as to form annular grooves 37 therebetween. Each one of the rings 36a–36e is formed with a small rib 38 extending laterally or radially outwardly therefrom. The wiping ribs 38 are easily deformable so as to fill any or all imperfections existing upon the interior surface of the battery bore 28 thereby creating a fluid-tight seal therewith, as will be fully described hereinafter.

At the lower end of the cylindrically-shaped member 30, there is provided a lead-in ring 40 disposed upon the outer surface thereof so as to assist in alignment of the hydrometer device with respect to the battery bore during the insertion of the hydrometer device 10 into the battery bore 28. As can be best seen from FIG. 4, the diameter of the lead-in ring 40 is slightly smaller than the diameter of the sealing rings 36a–36e. The lead-in ring 40 includes an inwardly sloping surface 42 which makes it possible for it to act as a guide as the collar 12 is being inserted into the battery bore 28. Without this lead-in ring 40, there may be a tendency for the collar to become misaligned vertically with respect to the battery bore upon insertion of the same into the battery bore.

In FIGS. 4 and 5, it can be seen that each wiping rib 38 is arranged substantially intermediate an upper surface 44 and a lower surface 46 of its respective sealing ring, FIGS. 4 and 5 specifically illustrating the lower-most sealing ring 36e. The wiping ribs 38 upon the sealing rings 36a–36e have a lateral dimension which in the undeformed condition (that is, prior to insertion) is slightly larger than the lateral dimension of the worst case or widest lateral dimension of the battery bore 28. The upper end of each wiping rib 38 is joined to the upper surface 44 of the respective sealing ring by means of a vertical landing 48 defining an indentation.

The longitudinal dimension of the vertical landing 48 may be substantially equal to one-half the distance defined between the upper and lower surfaces 44 and 46. In any event, the longitudinal dimension of this indentation must be of sufficient size so as to provide a space for accommodating the entire width of the wiping rib when it is deformed upon insertion of the collar into the battery bore. The lower end of each wiping rib is joined to the lower surface 46 of the respective sealing ring by means of an inwardly tapered or beveled surface 50. The lateral dimension of the lower surface 46 is slightly smaller than the lateral dimension of the upper surface 44.

Figure 6:
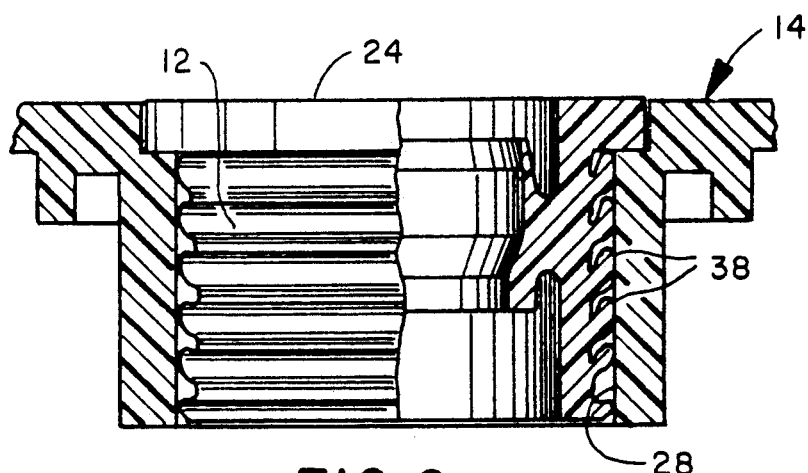
FIG. 6 is a fragmentary, cross-sectional view of the battery casing bore with the improved hydrometer collar of the present invention disposed therein.

FIG. 6 shows how the wiping ribs 38 are permanently deformed against the interior surface portions of the battery bore with a tight interference fit upon insertion of the improved hydrometer collar 12 into the battery bore. It should be noted that the wiping ribs will be yieldingly compressed into engagement with and conform to any imperfections such as, for example, scratches or voids existing upon the interior surface of the pre-formed battery bore 28 so as to fill in any areas that would have resulted in leakage of the battery fluid.

In view of the fact that there are wide tolerances in the lateral dimensions of the battery bore along its axial length even though the battery casings are manufactured in accordance with high industrial standards, it is necessary that the wiping ribs have the ability to compensate for substantial lateral variations in the bore of the battery and other irregularities. This function is achieved by means of the deformable nature of the material from which the collar is formed. The improved hydrometer collar 12 is preferably formed from a variety of deformable materials which are commercially available, such, for example, as polypropylene, polyethylene, resilient vinyl polymer and the like.

Figure 7:
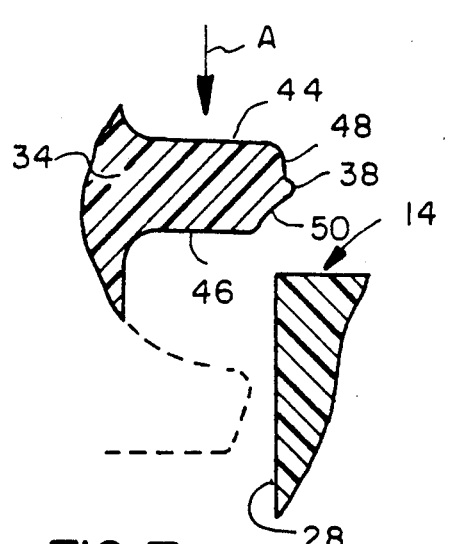
FIG. 7 is an enlarged, fragmentary view of the improved hydrometer collar and a battery bore having a relatively wide diameter before insertion of the hydrometer collar into the battery bore.
Figure 8:
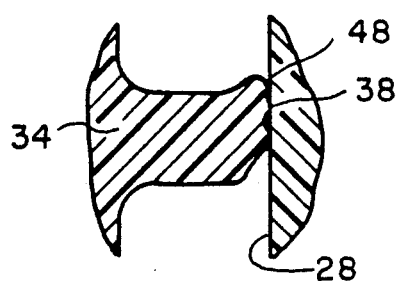
FIG. 8 is an enlarged, fragmentary view of the improved hydrometer collar and the battery bore of FIG. 7 after insertion of the hydrometer collar into the battery bore.

The operation of permanently deforming the wiping ribs so as to compensate for the lateral variations of the battery bore can be illustrated from FIGS. 7 through 10. FIG. 7 shows an enlarged, fragmentary view of the improved collar prior to insertion into a battery bore having a relatively wide diameter. As the collar is inserted into the bore by means of a force in the axial direction along the arrow A, each wiping rib 38 is permanently deformed so as to fill in a portion of the space along the vertical landing or indentation 48, as shown in FIG. 8.

Figure 9:
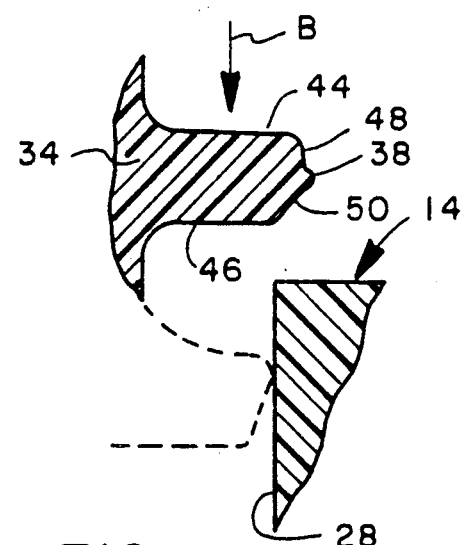
FIG. 9 is an enlarged, fragmentary view of the improved hydrometer collar and a battery bore having a relatively narrow diameter before insertion of the hydrometer collar into the battery bore.
Figure 10:
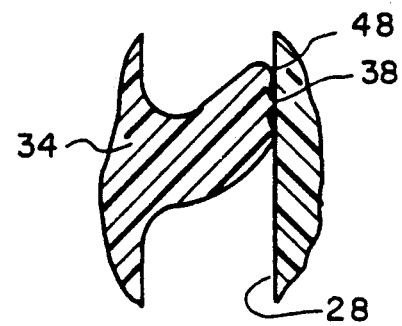
FIG. 10 is an enlarged, fragmentary view of the improved hydrometer collar and the battery bore of FIG. 9 after insertion of the hydrometer collar into the battery bore.

Similarly, FIG. 9 is an enlarged, fragmentary view of the improved collar 12 prior to insertion into a battery bore having a relatively narrow diameter. Again, as the collar is depressed into the bore in the direction of the arrow B, each wiping rib 38 is permanently deformed so as to completely fill the space along the vertical landing 48, as shown in FIG. 10. It will be seen that the above-described deformation operation of the wiping ribs achieves the objective of creating the fluid-tight interference fit with the interior surface of the varying-sized battery bores so as to provide a better seal therewith.

The improved hydrometer collar 12 of the present invention was constructed and tested by separately applying pressures to each one of the sealing rings 36a–36e having the wiping ribs 38 so as to determine if a particular rib permitted leakage. It was found that the rings with wiping ribs exhibited higher quality performance since they could generally withstand pressures up to 10 psi without experiencing a leak. In addition, even when one or more of the rings 36a–36e leaked, the collar 12 would still be acceptable as long as all of the rings did not leak. As compared to the collar of the type found in the '282 patent, the improved collar 12 of the present invention yielded a much better sealing operation or function.

From the foregoing detailed description, it can thus be seen that the present invention provides an improved battery hydrometer collar having a novel sealing means so as to provide a better seal upon insertion of the hydrometer into a pre-formed bore located within the top of a battery casing. The improved hydrometer collar of the present invention includes a small wiping rib integrally formed with each one of a plurality of sealing rings and extends radially outwardly therefrom. The wiping ribs are easily deformable so as to fill in any imperfections existing upon the interior surface of the battery casing bore of the storage battery into which the collar is inserted thereby creating a fluid-tight seal therewith.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

What is claimed is:

1. An improved hydrometer collar for use in lead-acid storage batteries of the type installed within vehicles, comprising:

a cylindrically-shaped member having an annular side wall;

a plurality of sealing rings being formed upon the outer surface of said annular side wall, each one of said plurality of sealing rings being spaced axially apart from each other in a substantially parallel relationship so as to form annular grooves therebetween and having an external peripheral surface; and a small wiping rib being formed integrally with each one of said plurality of sealings rings and extending radially outwardly from said external peripheral surface of a respective one of said sealing rings;

each one of said wiping ribs being disposed substantially intermediate an upper surface and a lower surface of a corresponding one of said plurality of sealing rings.

whereby said wiping ribs are easily deformable so as to fill in any imperfections existing in the interior of a battery casing bore of said storage battery into which said collar is inserted thereby creating a fluid-type seal.

2. An improved hydrometer collar as claimed in claim 1, wherein said wiping rib has an upper end connected to said upper surface of said sealing ring by means of a vertical landing defining an indentation and has a lower end connected to the lower surface of said sealing ring by means of an inwardly tapered surface.

3. An improved hydrometer collar as claimed in claim 2, wherein said indentation has a dimension sufficient to provide a space to accommodate the width of said wiping rib when it is deformed upon the insertion of said collar into the battery casing bore.

4. An improved hydrometer collar as claimed in claim 1, wherein the lateral dimension of said wiping ribs in the undeformed condition is slightly larger than the lateral dimension of the battery casing bore.

5. An improved hydrometer collar as claimed in claim 1, wherein said wiping ribs are formed of a deformable material.

6. An improved hydrometer collar as claimed in claim 5, wherein said deformable material is polypropylene.

7. An improved hydrometer collar as claimed in claim 1, wherein said collar is formed of a deformable material.

8. An improved hydrometer collar as claimed in claim 1, further comprising a lead-in ring disposed on the outer surface of said annular side wall at the lower end of the said cylindrically-shaped member so as to assist in alignment during insertion of said collar into said battery casing bore.

9. An improved hydrometer collar as claimed in claim 8, wherein the diameter of said lead-in ring is slightly smaller than the diameter of said plurality of sealing rings.

10. For use in lead-acid storage batteries of the type installed within vehicles, an improved hydrometer collar for creating a fluid-tight seal comprising, in combination:

a cylindrically-shaped member having an annular side wall;

a plurality of sealing rings being formed upon the outer surface of said annular side wall, each one of said plurality of sealing rings being spaced axially apart from each other in a substantially parallel relationship so as to form annular grooves therebetween and having an external peripheral surface; and a small wiping rib being formed integrally with each one of said plurality of sealing rings and extending radially outwardly from said external peripheral surface of a respective one of said sealing rings;

each one of said wiping ribs being disposed substantially intermediate an upper surface and a lower surface of a corresponding one of said plurality of sealing rings, whereby said wiping ribs are easily deformable so as to fill in any of said irregularities existing in the interior surface of said battery casing bore of said storage battery into which said collar is inserted thereby creating a fluid-tight seal.

11. An improved hydrometer collar as claimed in claim 10, wherein said wiping rib has an upper end connected to said upper surface of said sealing ring by means of a vertical landing defining an indentation and has a lower end connected to the lower surface of said sealing ring by means of an inwardly tapered surface.

12. An improved hydrometer collar as claimed in claim 11, wherein said indentation has a dimension sufficient to provide a space to accommodate the width of said wiping rib when it is deformed upon the insertion of said collar into the battery casing bore.

13. An improved hydrometer collar as claimed in claim 11, wherein the lateral dimension of said wiping ribs in the undeformed condition is slightly larger than the lateral dimension of the battery casing bore.

14. An improved hydrometer collar as claimed in claim 11, wherein said wiping ribs are formed of a deformable material.

15. An improved hydrometer collar as claimed in claim 14, wherein said deformable material is polypropylene

16. An improved hydrometer collar as claimed in claim 11, wherein said collar is formed of a deformable material.

17. An improved hydrometer collar as claimed in claim 11, further comprising a lead-in ring disposed on the outer surface of said annular side wall at the lower end of the said cylindrically-shaped member so as to assist in alignment during insertion of said collar into said battery casing bore.

18. An improved hydrometer collar as claimed in claim 17, wherein the diameter of said lead-in ring is slightly smaller than the diameter of said plurality of sealing rings.

19. An improved hydrometer collar as set forth in claim 8, wherein:
   said lead-in ring includes an inwardly sloping surface for guiding said collar into said battery casing bore as said collar is inserted into said battery casing bore.

20. An improved hydrometer collar as set forth in claim 17, wherein:
   said lead-in ring includes an inwardly sloping surface for guiding said collar into said battery casing bore as said collar is inserted into said battery casing bore.

* * * * *